United States Patent [19]

Gabello et al.

[11] Patent Number: 5,847,753
[45] Date of Patent: Dec. 8, 1998

[54] CAMERA SYSTEM FOR SCANNING A MOVING SURFACE

[75] Inventors: Louis R. Gabello, Rochester; Leon Robert Zoeller, Hamlin; James P. Guy, Rochester, all of N.Y.

[73] Assignee: Eastman Kodak Company, Rochester, N.Y.

[21] Appl. No.: 99,289

[22] Filed: Sep. 24, 1993

Related U.S. Application Data

[63] Continuation-in-part of Ser. No. 047,325, Apr. 16, 1993, abandoned.

[51] Int. Cl.[6] ............................................... H04N 7/18
[52] U.S. Cl. ............................... 348/88; 348/92; 348/125
[58] Field of Search ............................... 348/88, 92, 132, 348/86, 91, 94, 359, 125, 128; 382/141; 364/550, 552

[56] References Cited

U.S. PATENT DOCUMENTS

| | | | |
|---|---|---|---|
| 4,561,103 | 12/1985 | Horiguchi et al. | 348/88 |
| 4,918,522 | 4/1990 | Pajunen | 348/132 |
| 4,922,337 | 5/1990 | Hunt et al. | 348/92 |
| 4,951,223 | 8/1990 | Wales et al. | 348/88 |
| 4,977,449 | 12/1990 | Morgan | 348/159 |
| 5,033,095 | 7/1991 | Marcantonio | 348/88 |
| 5,239,376 | 8/1993 | Dittmann et al. | 348/88 |

OTHER PUBLICATIONS

Fiber Optics and Video: A Background, George F. Benton, SMPTE Journal, Jul. 1988, pp. 546–555.

*Primary Examiner*—Tommy P. Chin
*Assistant Examiner*—Vu Le
*Attorney, Agent, or Firm*—Thomas H. Close

[57] ABSTRACT

A camera system utilizes a line scan (linear array) camera designed to scan a moving surface and subsequently to generate and to transmit a high quality digitized video signal over a long a distance by an optical fiber. The primary function of the system is: to scan a moving surface using a 2048 or a 1024 linear array; to condition and digitize the array analog video signal; and subsequently to transmit to a computer processing unit, without a noticeable loss in fidelity, the digitized video data over a long distance by means of an optical fiber connected to the camera and the computer processing unit. The system also functions to transmit both video signals and non-video information signals over a fiber optic link from the camera to the computer processing unit.

31 Claims, 5 Drawing Sheets

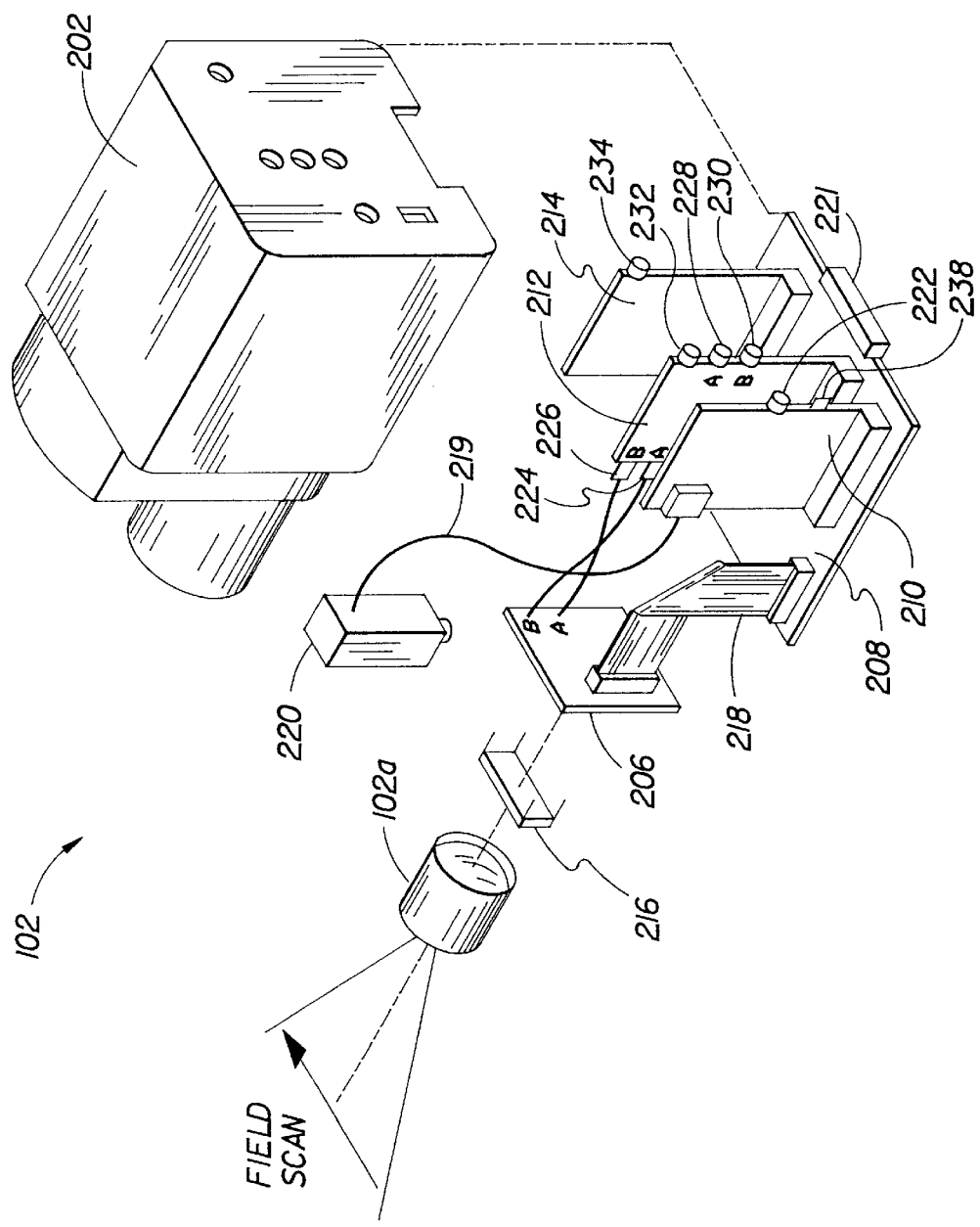
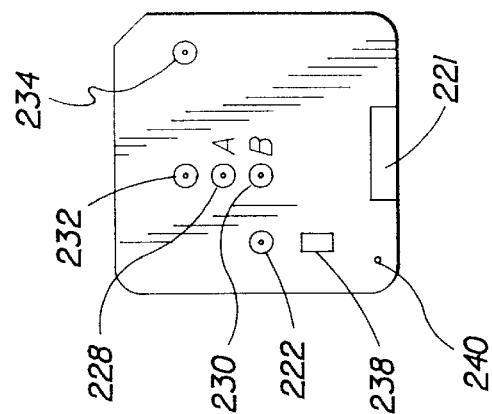
FIG. 2
FIG. 2A

| FRAME NUMBER(S) | 1 | 2 | 3-695 | 696-697 | 698 | 699-703 |
|---|---|---|---|---|---|---|
| | START/ STATUS | COMMAND | VIDEO DATA | EXTERNAL DATA WEB POSITION DATA EVENT DATA | CHECK SUM | SYNC |

DATA STREAM FORMAT

FIG. 5

CAMERA SYSTEM FOR SCANNING A MOVING SURFACE

This is a Continuation-in-Part Application of U.S. patent application Ser. No. 047,325, filed Apr. 16, 1993, now abandoned.

FIELD OF THE INVENTION

The present invention relates to a system for inspecting a product by scanning a surface of the product with a scanning device and transmitting video signals as well as information signals generated external to the scanning device along a common fiber optic link to a processing unit. More particularly, the invention relates to a system for inspecting a moving continuous sheet product during manufacturing using a stationary linear charge coupled device (CCD) camera which generates video signals associated with a surface of the product, and then transmits the video signals along with externally generated information signals along a single fiber optic link to a computer processing unit.

BACKGROUND OF THE INVENTION

In the related art, camera systems are utilized for scanning moving surfaces, such as web production lines, in order to monitor and analyze the moving surface for quality control purposes. For instance, a moving surface such as a continuous production line of photographic paper may be passed in front of a camera system for the purpose of scanning the photographic paper for defects. The defects could include dark spots on the photographic paper. In this example, the related art typically has a camera connected to a processing unit such as a computer mainframe. The camera, which is placed in a position to scan the moving surface, provides data about the scan, generally in the form of an analog video signal. This analog video signal is typically transmitted to a computer processing unit by a wire cable.

With respect to the analog video signal, the bandwidth of this signal tends to diminish as the length of the wire cable increases. This bandwidth diminution of the analog video signal places a limitation on the distance that the camera, which is positioned in the vicinity of the scanned moving surface, can be placed in relation to the computer processing unit. As such, the computer processing unit is generally subjected to the harsh environment typically experienced in the proximity of a manufacturing production line. Typically, installing the computer processing unit in an air conditioned environment is considered beneficial.

One approach to overcome the bandwidth diminution over increasing distances of a wire cable is to digitize the analog video signal. The digitized signal is then transmitted from the camera over a wire cable to the processing unit as a digitized differential signal to help eliminate common mode noise. However, transmitting a differential signal tends to increase the number of wires required in the wire transmission cable by a factor of eight (for eight-bit A/D conversion). This increase in the number of wires is generally not a significant problem over small distances such as 8 meters. However, the length of the increased number of wires encountered when using this approach not only tends to add significant costs but also continues to limit the bandwidth over long distances such as 1,000 meters.

In addition to video signals, it is also necessary to transmit other information to the processing unit. These other information signals, which are usually generated externally to the camera, may include information related to the position or speed of the web in order to facilitate identification of the position of the web where a defect exists, for example. The information may indicate the beginning or end of a web roll, or may include a command signal to divert or sort the product being inspected. In short, this other information can reveal any number of characteristics or parameters about the product being inspected.

Problem to be Solved by the Invention

A need has therefore been felt for a system that can scan a moving surface, such as a continuous production line of photographic paper, and subsequently transmit video data obtained from the scan, over a distance to a computer processing unit, wherein the transmission distance is long enough to permit the positioning of the computer processing unit in an environment which is different than the environment of the moving surface, but in such a way so as not to lose transmitted signal fidelity, which loss in fidelity is predominantly caused by bandwidth diminution over long distances. A need has also existed to transmit both video data, as well as information usually generated externally to the camera which produces the video data, to the remote processing unit.

SUMMARY OF THE INVENTION

It is therefore an object of the present invention to provide a system which scans a moving surface and transmits a video signal to a computer processing unit over a long distance, for example, greater than 1,000 m. It is also an object of the present invention to provide a system which scans a moving surface and transmits both a video signal and an information signal along a single optical fiber to a computer processing unit.

It is a feature of the present invention to provide a system which utilizes a line scan (linear array) camera designed to scan a moving surface and subsequently to generate and to transmit a high quality digitized video signal over a long distance by means of fiber optic cable connection. The present invention eliminates the need to transmit a digitized differential signal. Instead, the present invention converts a digitized signal into a formatted data stream for transmission over long distances by means of a single fiber. The primary function of the system is: to scan a moving surface using a 2048 or a 1024 linear array; to condition and digitize the array analog video signal; and subsequently to transmit to a computer processing unit, without a noticeable loss in fidelity, the digitized video data over a long distance by means of a fiber optic cable connected to the camera and the computer processing unit.

It is also an object of the present invention to provide a method for inspecting a product, comprising the steps of: scanning a surface of the product with a scanning device (e.g., a linear array charge coupled device camera) and creating video data signals corresponding to the surface, generating information signals related to the product, where the information signals are created external to the scanning device, transmitting both the video data signals and the information signals along at least one optical fiber to a computer processing unit, and processing the video data signals and the information signals to evaluate the condition of the product. In a preferred embodiment, the system transmits both video and information signals during each scan line (if there is information to be transmitted). Since information signals are transmitted before a subsequent line segment of the surface is scanned, the time required to transmit the combined signals is minimized. An apparatus to implement the method is disclosed and claimed.

Advantageous Effects of the Invention

A preferred embodiment of the present invention for scanning a moving surface is a camera system comprising: a processing unit which generates control signals and receives transmitted data signals; a camera responsive to said control signals and providing said data signals in response to said moving surface, said camera mounted in fixed spatial relationship with respect to said moving surface; and a high fidelity optical fiber coupled to said camera and to said processing unit, said fiber optic cable providing a pathway through which to transmit said control signals and said data signals between said camera and said processing unit over a first distance. The preferred embodiment also includes means for generating information signals externally to the camera, which information signals relate to various characteristics and/or parameters of the product or object being scanned. The camera also comprises means for multiplexing the video and information signals to form a sequential stream of data which is then transmitted to the computer processing unit.

An advantage of the present invention is that the distance between the camera and the computer processing unit can be increased with a negligible diminution in the bandwidth of a transmitted analog video signal.

Another advantage of the present invention is that the computer processing unit can be maintained in an environment (such as an air conditioned room) which is separate from the environment that the camera must be subjected to.

Another advantage of the present invention is that a plurality of cameras can be utilized with a centrally located computer processing unit, such that one camera can be focused on each of a plurality of different surfaces, or the plurality of cameras can each be focused on a single surface for greater resolution, or any combination thereof.

A further advantage is that only a single fiber optic link is required to transmit both video and non-video (information) signals from the camera to the processing unit.

Still a further advantage is that the system utilizes normally non-useful or dead video pixels (e.g., dark pixels) to transmit non-video (information) signals, thereby minimizing the time required to transmit the combined video and non-video signals.

Further, a preferred embodiment of the present invention has a camera controller which provides power and control signals for a plurality of cameras and is intended to be located in the vicinity of the camera at the production line. This camera controller can be connected via a serial fiber optic link to the computer processing unit, thereby forming a complete front-end closed loop system which can permit a user to operate the camera at the production line or at the computer processing unit.

BRIEF DESCRIPTION OF THE DRAWINGS

The advantages and features of the present invention will become better understood with reference to the following more detailed description and claims taken in conjunction with the accompanying drawings in which like elements are identified with like symbols and in which:

FIG. 2 is an exploded view showing the internal primary structure of the camera of FIG. 1;

DESCRIPTION OF THE PREFERRED EMBODIMENTS

1. Detailed Description of the Figures

Figure 1:
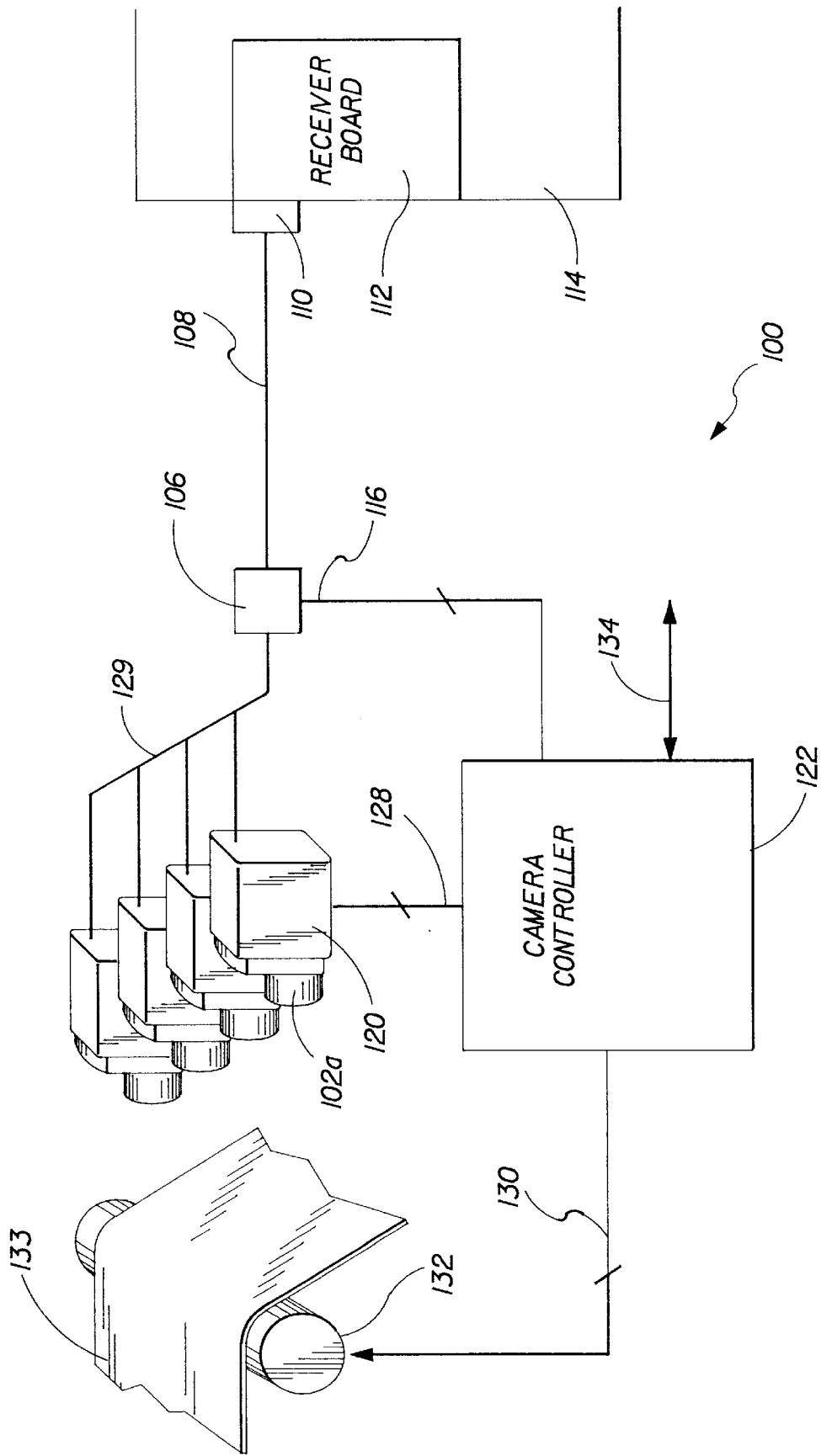
FIG. 1 is an overall block diagram of a preferred embodiment of the present invention which utilizes a camera, a computer processing unit, and a camera controller each connected with a fiber optic connection to form a complete front-end closed loop system.

Referring now to FIG. 1, a block diagram of a preferred embodiment of a camera system 100 is shown, according to the present invention. A camera 102 with a lens 102a is connected by an optical fiber 129 through a junction box 106 to a length of fiber optic cable 108 (trunk cable), which generally ranges in length from 15 meters to 5,000 meters and typically exceeds a length of 30 meters. The other end of the fiber optic cable 108 is connected at a junction box 110 to a receiver board 112 which has been integrated with a computer processing unit 114 for the purposes of receiving fiber optic data transmissions. It is to be noted that, in a preferred embodiment, a camera (more particularly, a linear array charge coupled device camera) is used as the scanning device. However, the patentees wish to expressly suggest that other scanning devices, e.g., lasers, might also be suitable to implement the method of the invention.

The length of fiber optic cable 108 typically consists of multiple optical fibers, each having a 62.5 μm fiber core. These fibers are individually terminated within each of the junction boxes 106, 110 by means of an ST connector. Cable 108 connects to the computer processing unit 114 by means of the fiber junction box 110 and to a camera controller 122 by means of a cable 116, which typically consists of a single optical fiber having a 62.5 mm fiber core. The cable 116 is connected to the fiber junction box 106. The fiber junction boxes 106, 110 serve to provide less disturbance to the fiber optic trunk cable 108 while allowing distribution and access to the individual fibers at the camera controller 122.

The camera controller 122, which supports operations of the camera 102, is intended to remain positioned in the vicinity of the camera 102 and is thereby connected to the camera 102 by a cable typically less than 8 meters in length. In a preferred embodiment of the present invention, the camera controller 122 provides power, control signals and data for up to 4 cameras 102 using a cable 128 consisting of 12 twisted shielded pairs for each camera 102. Video output from the camera 102 is transmitted though the individual fibers 129 to the junction box 106 for transmission to the processing unit 114.

The camera controller 122 can receive an input signal 130 from an external encoder 132 positioned in the proximity of an inspection product 133. The encoder 132 enables web position and speed determinations as well as exposure/scan rate synchronization. An optically isolated digital I/O signal 134 provides the ability for the camera controller 122 to acquire external status information such as beginning-of-roll, end-of-roll, and control auxiliary operations such as a sort command.

Referring now to FIG. 2, an exploded view of the video camera 102 is shown. A camera housing 202, equipped with a lens 102a, encloses and protects an array board 206, a mother board 208, a viewfinder board 210, a video board 212, and a transmitter board 214. A moving surface in front of the lens 102*a* is scanned in the scan field of the lens 102*a* which transmits the scanned image to a linear array 216. This linear array provides analog video signals to the array board 206 which is mounted behind the front lensing section of the camera. The array board 206 receives power and timing signals from the mother board 208 via a ribbon cable 218.

The optional viewfinder board 210 is coupled to the mother board 208 and receives a standard RS-170 video input 219 from an optional viewfinder camera 220. The optional viewfinder camera 220 is well-known in the art and manufactured by an original equipment manufacturer (OEM) such as the Sony Corporation. The viewfinder board also provides a viewfinder output to a viewfinder output terminal 222 which is used to transmit video data from the viewfinder camera 220 to the camera controller 122 (shown in FIG. 1) for observation by the user. A terminal 222 allows the user to obtain viewfinder video output directly from the rear of the camera housing 202.

The video board 212 is coupled to the mother board 208 and receives video signal inputs 224 (video A) and 226 (video B) from the array board 206. The video board 212 provides additional conditioning of the video signals A and B from the array board 206 prior to being converted from an analog signal to a digital signal (A/D conversion). The video board 212 provides a video output terminal 228 for video A, a video output terminal 230 for video B and an output terminal 232 for an external synchronization signal. Terminals 228, 230 are for the user to observe the conditioned video signals A and B. The terminal 232 is for an array START signal that is provided as an external synchronization signal for triggering an oscilloscope.

The transmitter board 214 is coupled to the mother board 208 and provides a fiber optic output terminal 234.

Finally, the mother board 208 is equipped with a pin connector 221 for use in connecting the mother board to the camera controller 122 with cable 128.

FIG. 2A shows the rear view of the camera housing through which the following terminals are accessed: SYNC output terminal 232; fiber optic output terminal 234; video output terminal 228; video output terminal 230; viewfinder output terminal 222; and auxiliary access 238; a reset access aperture 240; and the pin connector 221.

Figure 3:
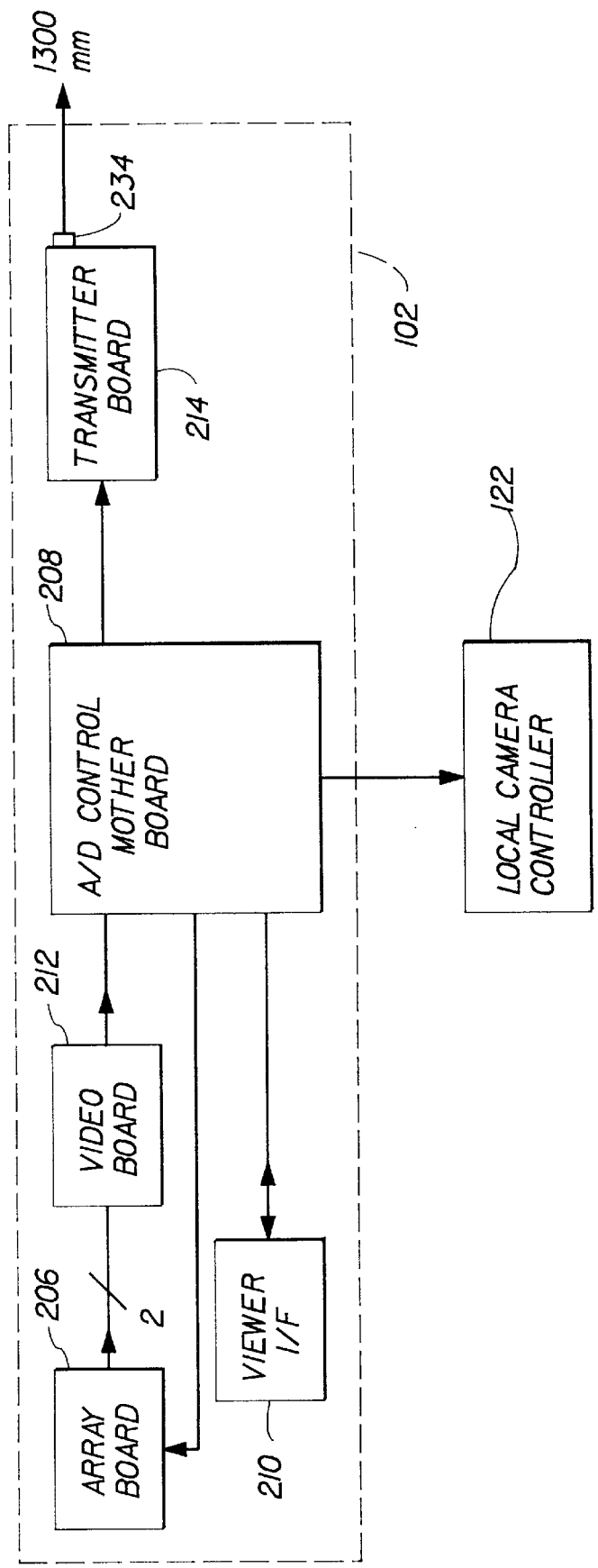
FIG. 3 is a more detailed block diagram of the camera shown in FIG. 1, including the output data signal of the camera and the connection to the proximately located camera controller.

Referring now to FIG. 3, a functional block diagram of the boards internal to the video camera 102 is shown with a connection to the camera controller 122. The array board 206 drives the linear array 216 (shown in FIG. 2) and performs correlated double sampling (CDS), which is a technique well-known in the art whereby a sampled analog reset reference level of a video channel in an array is subtracted from the video signal within a timeframe of one pixel. Assuming that the same or similar noise exists due to close intervals of sampling, subtraction of the (reset reference level+noise) from the (video signal+noise) results in: (video+noise)−(reset reference level+noise)=video−reset reference level. Therefore, residual noise is minimized or eliminated by using the technique of CDS.

The video board 212 performs d-c restoration and amplification. The mother board 208 performs analog to digital (A/D) conversion, data stream formation, serial interface (I-F), and diagnostics. The mother board also provides use of an optional viewfinder board 210 as shown in FIG. 2. The transmitter board 214 provides a 40 bit parallel to serial conversion, data encoding (NRZI, 4*b*/5B), and an ECL drive of a 1300 nm diode at the fiber optic output terminal 234. It is well-known in the art that "non-return to zero, inverted"

(NRZI) is a coding scheme where all 1's in a data stream are represented by a level transition and all 0's are represented by no transition. It is further well-known in the art that 4*b*/5B encoding refers to a method of using a grey code to transform 4 binary bits to 5 binary bit intervals (5 Baud) when transmitted; the purpose is to guarantee a higher degree of sequential level transitions in the serially transmitted data. This higher modulation is needed on the a-c coupled optical link to maintain a proper reference level.

Transmission of Video and Control Data Over Fiber Optic Link

As described previously, for complete web inspection, other information external to the camera is often needed by the mainframe computer processing unit from the front-end of the system (camera installation area on the web.) Examples of this information include, for example, a) The down-web position of the material and, b) Control data from web monitoring devices. Down-web position and its rate of change can be derived from an encoder geared to a web roller. From the encoder, web speed can be determined along with the position of imperfections or defects found in the web. Control data could include a TTL logic level flag associated with the beginning-of-roll or end-of-roll. A command issued to divert or sort web material is another example of control information. In essence, control data could indicate any number of characteristics or parameters about the product being inspected. Control data and encoder information enable the mainframe to identify web position and occurrence of various events. Thus, it is seen that three key types of information provided to the signal processing mainframe are: a) video data corresponding to the scanned surface, b) position information and c) external control data.

Obviously, coupling the "non-video" data to the mainframe could be accomplished using wire cables. For example, encoder signals could be transmitted via twisted shielded pairs to the interface within the mainframe chassis. The present invention, however, uses the single optical fiber which carries the video signal to the mainframe to also transmit the non-video control signals as well, thereby eliminating the need for added parallel wires. The method used by the invention to transmit both the video and-non-video data involves multiplexing data from the front-end (camera location) in such a way as to form a sequential stream of data transmitted to the mainframe. Moreover, a common feature of linear CCD arrays is that there are normally latent periods (or dead spaces) which occur before and after valid video within one scan line. The present invention utilizes these latent periods to transmit the non-video information. In this way, the time required to transmit the combined information is minimized.

Figure 4:
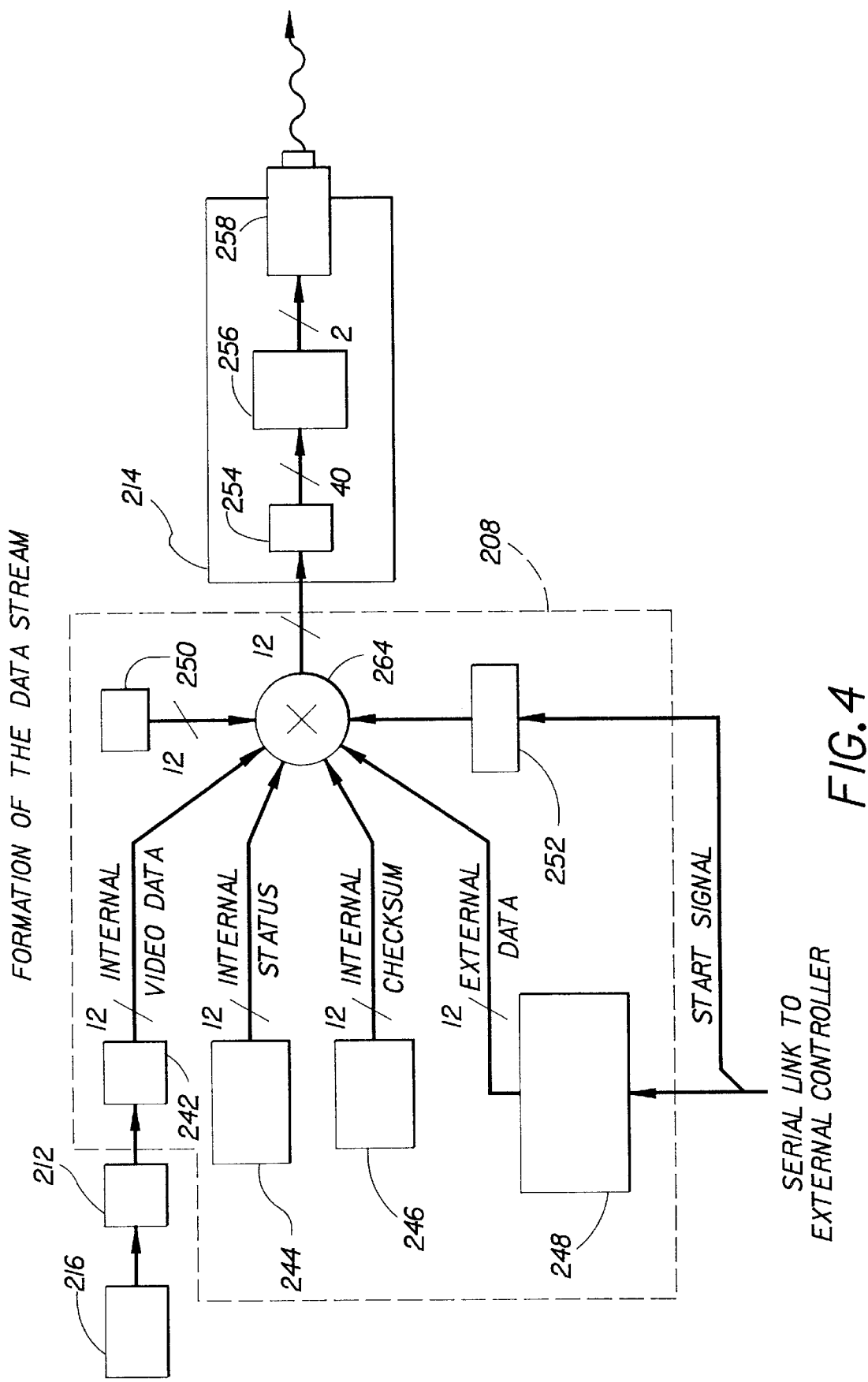
FIG. 4 illustrates how the video data and non-video (information) data are combined within the camera to form a sequential data stream; and, FIG. 5 illustrates the data stream format for a camera having 2048 valid video pixels.

FIG. 4 illustrates in block diagram form how the various sources of data are combined within the camera to form the sequential data stream. Initially, linear array 216 is exposed to light reflected from the surface of a linear segment of the product being inspected. The time during which the array is exposed is defined to be the "exposure time interval". This analog video signal is then sent to video board 212 (via array board 206, not shown in FIG. 4) for additional conditioning. The conditioned signal is then sent to A/D converter 242 within mother board 208. The mother board contains five (5) sources of data, including video data from A/D converter 242; internal status data from internal status register 244; internal checksum data from checksum devices 246; external data from external data FIFO memory 248; and null data from null data register 250.

The data from devices 244, 246, 248 and 250 is both individually and collectively referred to as "non-video" or "informational" signals or data. The internal status register, for example, stores an indication of commands sent to the camera. An example would be a command sent from the computer processing unit to turn on a test pattern. The checksum devices calculates an arithmetic sum of all previous tri-nibbles (hereinafter referred to as a "tribble" which abbreviates "tri-nibble") of information sent. This calculation is performed at the transmitter end, and a corresponding calculation is done at the receiving end. If the arithmetic sums at the transmitter and receiver do not match, one would know that a transmission problem occurred, and that data may have been lost. The external data register stores external command data issued to the camera, as well as externally generated web position data and external event data. The null register stores data of zero value, which are useful to "fill" empty frames (since the system transmits three frames at a time, it is sometimes necessary to fill an empty frame with zeros in order that the three frames can be transmitted.)

Typically, the start signal and external information are received by the camera from an external controller. The START signal initiates the sequence hardware within the camera. The sequence determines which source of data is coupled into the transmitter while the array is being read out. As shown, sequencer 252 (Altera Corporation Model EPM5032 EPLD, or equivalent) selects among internal camera status, video data, external data (command, web position, external events), null and checksum. Note that each source of data consists of 12 bits per pixel (i.e., a tribble.) Conceptually, the sequencing may be considered to be a form of multiplexing accomplished by multiplexer 264.

Three consecutive tribbles are combined within transmitter 214 along with four qualifier bits to form a "FRAME" (each frame comprises 40 bits.) The tribbles and qualifier bits are stored in registers 254 within the transmitter and are then formatted by high speed formatter 256 (Gazelle HOT ROD™ High Speed Serial Link Gallium Arsenide Chipset [Transmitter GA9011 and Receiver GA9012], or equivalent) and finally transmitted by 1300 nm fiber optic transmitter 258 (AT&T Model ODL 200 Lightwave Data Link With Flag, or equivalent.) The transmitter encodes and transmits on a frame by frame basis.

FIG. 5 shows the data stream format. Transmission begins with frame number one. For a linear array having 2048 valid pixels, 703 frames are transmitted. Note that the array readout begins with frame number one; while the array is shifting out non-video pixels, other information in frames 1 and 2 are transmitted in order to occupy the otherwise useless frames.

Table 1 below describes the formation of the transmitted data stream. The table specifically identifies the frame number and associated tribbles in proper sequence. "Null" tribbles are of zero value and provide completion of frame separated by function. The checksum frame provides validation of the entire line of valid data.

TABLE 1

12 bit (tribble) sequences are processed into the transmitter; three sequential tribbles constitute one frame of input data. The sequence shown in FIG. 5 and described below is for a 2048 pixel array; a 1024 array sequence is also selectable.

| | |
|---|---|
| frame 1 | 1 null |
| | 2 null |
| | 3 STATUS |
| frame 2 | 4 null |
| | 5 null |

TABLE 1-continued 12 bit (tribble) sequences are processed into the transmitter; three sequential tribbles constitute one frame of input data. The sequence shown in FIG. 5 and described below is for a 2048 pixel array; a 1024 array sequence is also selectable.

| | |
|---|---|
| frames 3–12 | 6 COMMAND |
| | 7 null |
| | . |
| | . |
| | . |
| | 36 null |
| frames 13–695 | 37 digitized video |
| | . |
| | . |
| | . |
| | 2084 digitized video |
| | 2085 null |
| frame 696 | 2086 external data (web position MSB) |
| | 2087 external data (web position MSB-1) |
| | 2088 external data (web position MSB-2) |
| frame 697 | 2089 external data (web position LSB) |
| | 2090 external data (event MSB) |
| | 2091 external data (event LSB) |
| frame 698 | 2092 null |
| | 2093 checksum 2 (MSB) |
| | 2094 checksum 1 (LSB) |
| frames 699–703 | 2095 null data, sync |
| | . |
| | . |
| | . |
| | 2108 null data, sync |
| | 2109 End of Line |

Flow of Transmitted Data Through the Fiber Optic Camera

1. A START signal initiates the readout of the Linear CCD array on the array board to produce unconditioned video proportional to the light intensity of the surface being scanned by the camera.
2a. The video signals are conditioned on the video board in preparation for digital conversion by the A/D converters using the following analog process; correlated double sampling, dc restoration, gain adjustment and, lastly, offset adjustment.
2b. The conditioned video is digitized to 12 bits by the two A/D converters on the mother board forming a successive stream of digitized pixels.
3. A stream of data to be transmitted is constructed by appropriately gating a register or memory on and feeding the data into the transmitter. The transmission of the data stream commences coincident with the START of the array, as in item 1 above. Refer to Table 1. The table shows the successive tribble sequence; three successive tribbles constitute a frame of valid data.
4. On the transmitter board, successive tribbles are received by one of three registers. After three tribbles are received (36 data bits), a frame transfer is initiated.
5. A frame transfer commences by loading the three tribbles and four auxiliary bits (totaling 40 bits) into a high speed formatter.
6. The formatter receives the 40 bits into an internal register. The data is encoded (4B/5B), serialized and converted to a differential signal (ECL level) for input to the infrared transmitting diode.
7. The output of the transmitter diode is coupled into an optical fiber for conveyance to a fiber optic receiver board in the mainframe.
8. At the receiver board, the transmitted light from the fiber is received by a high speed photodetector; the output of the detector is a serial ECL signal representing the data.

9. The serial ECL differential signal is fed into a deformatting receiver which converts the signals back to a TTL level, deserializes the data, decodes the data and presents a registered parallel output of 40 bits to the subsequent processing logic. The 40 bits are comprised of the three tribbles and 4 auxiliary bits. The auxiliary bits are used to provide verification of the first valid transmitted data frame.

2. Operation of the Preferred Embodiments

The camera system 100 as shown in FIGS. 1 and 2, includes a plurality of digital video cameras 102 along with the camera controller 122, the optional viewfinder camera 220, optical fibers 108, 116, 129, and cable 128, fiber junction boxes 106, 110, and the computer processing unit 114 with the accompanying receiver board 112. The primary function of the camera system 100 is to scan a moving surface using a 2048 or a 1024 linear array 216, to condition and to digitize the resulting array video signal and subsequently to transmit the video data over a long distance to the computer processing unit 114 without substantial loss in fidelity of the signal. Speed, long distance and high video integrity are parameters targeted by design. In a preferred embodiment, the system can accommodate 9483 lines per second for a 2,048 array or 18,433 lines per second for a 1,024 array. Video signals are resolved to 12 bits; data transmitted over a 1,000 meter distance is accomplished with a 250 megabaud fiber optic interface 234 designed into each video camera 102. In a preferred embodiment, typical performance accommodates a distance of 1,000 meters with design expectations of 5,000 meters with a $10^{-12}$ bit error rate.

Supporting the camera 102 operations is the proximately located camera controller 122; this controller is intended to be utilized within 8 meters of the camera 102. The controller provides power, control signals and data for a plurality of cameras using a cable 128 consisting of 12 twisted shielded pairs for each camera. The control signals (START, DATA, DATA CLOCK) provide for multi-camera synchronization, exposure control, and serial transfer of control data. Control data consists of operating commands, digital I-O status and web position data. Each START pulse from the controller is accompanied by the serial transmission of control data. In addition, each START pulse initiates readout of the linear array 216 and transmission of data (both video and control signals) to the receiver board 112 of the computer processing unit 114. As a result, the control data is concurrent with the video scan line. Exposure levels are directly influenced by the START interval established via the controller 122. This interval can be linked to an external encoder 132 or derived from an internal clock within the controller 122. Additionally, the cameras can be controlled at the same or different scan rates and operating modes as determined by the user through the controller 122. Use of an external encoder for a web enables a direct correspondence between web position and the scan line, thus providing a constant down-web pixel size.

The controller 122 also provides an interface to peripherals and the computer processing unit 114. The processing unit 114 can communicate with the controller 122 over a fiber optics RS-232 interface from the fiber junction box 106. Accordingly, the camera 102 may be remotely controlled via a computer terminal located at the computer processing unit 114. Further, a computer terminal located at the controller 122 accommodates local operations of the camera 102. Either terminal can access the controller to establish the operating or diagnostic mode. The processing unit 114 can be informed of or verify mode changes by RS-232 or by echoed command information encompassing each line of transmission.

The controller 122 provides an interface for the external encoder 132 which enables web positions and speed determinations as well as exposure/scan rate synchronization. The optically isolated digital I-O signal 134 provides the ability to acquire external status information such as beginning-of-roll, end-of-roll, and control auxiliary operations such as sort command (which is connected to switches or control points (not shown) on the production line.)

A feature of the controller 122 is the availability of grey level video. Each camera 102 has the option of containing an internal two-dimensional web view camera. The resulting RS-170 video can be accessed at a connector at the rear of the camera. The video is also sent to the controller 122 where the user can selectively view a desired channel on the local grey scale monitor. The viewer can be helpful for alignment purposes in that it presents not only video but also a horizontal cursor representing the array sensor position superimposed upon the real-time web view.

The processing unit 114 and the controller 122 are connected by means of the cables 108 and 116 junctioned at junction box 106; fiber termination at each end of cable 108 is accomplished using ST connectors within the fiber junction boxes 106, 110. The boxes serve to provide less disturbance to the fibers of the trunk cable 108 while allowing distribution and workability of the individual fibers at the controller 122 and the camera 102 site. Fibers are available for camera data, optical RS-232, fast link, RS-170 grey-scale video (optional).

The fast link is a direct binary link provided for communicating high speed digital flags requiring minimum delay time from the processing unit 114. An example is the generation of the sort command to the controller 122 based upon processed video data. The controller 122 would respond by issuing a signal to divert the targeted web sheet. The signal would be coupled externally from the controller 122, through the input signal 134 for isolation purposes. A command to sort issued to the controller 122 using fast link would minimize delay and help to prevent an incorrect sheet from being chosen. An interrupt signal issued from the processing unit 114 to the controller 112 would be another application of the fast link. The closed loop control of the camera system 100 enables capability of evaluating performance. Within the camera 102 are diagnostic modes allowing repeated data patterns. The transmission data value and position within the data stream can be consistently given. Thus, the integrity of the camera and fiber communications can be analyzed. Other diagnostic commands provide simple separation of functionality within the controller 122 and the camera 102.

Referring to FIG. 2 for the operation of the camera 102, a moving surface in front of the lens 102a is scanned and a video signal is derived from the linear array 216 on the array board 206. This board receives power and timing signals from the mother board 208 via the ribbon cable 218. The timing signals include: a) START signal: and b) the read out pixel clock. Upon receiving the START signal, the linear array 216 alternatively shifts out the acquired video signals on two channels as A and B video. The video is conditioned by performing a correlated double sampling of each pixel. The operation of correlated double sampling (CDS) mitigates noise; video and noise are correlated within the one pixel time window. This operation establishes a video level relative to the channel reset reference level (at that moment) thus minimizing any error attributed to spurious level shifts. The resulting video signals are buffered and connected to the video board 212 at video signal inputs 224, 226.

The video board 212 provides additional conditioning of the array video signal prior to A/D conversion. The video-A and video-B signals from the array board 206 initially pass through a gain amplifier stage. A gain adjustment is performed to calibrate the plurality of cameras to an expected value from the A/D converter established as the standard. Following amplification, the video signals are d-c restored to remove the expected high voltage shifts from the previous processing components as well as any undesired d-c variations attributed to normal component differences or integrated dark current levels. A buffering stage provides a calibration offset adjustment to compensate for the zero referenced A/D converter. The resulting conditioned video signals are transmitted to the mother board 208 for conversion. In addition to video conditioning, the video board contains circuitry which sets the input voltage range on each A/D converter. The conditioned video signals are also buffered and connected to external video output terminal 228, 230 for observation by the user. A start signal for the linear array 216 also provides an external synchronization signal at the SYNC output terminal 232 for triggering an oscilloscope.

The mother board 208 provides power and control signals for the daughter boards: array board 206, video board 212, transmitter board 214, and viewfinder board 210. External control signals and power are delivered from the controller 122 by the cable 128 (both shown in FIG. 1) connected to the pin connector 221 on the bottom of the mother board.

In a preferred embodiment, external control signals consist of the external start, data clock, data, reset and viewer-on; the external start, data and data clock are differentially driven signals. The basic timing of the camera 102 centers around the external start signals received over the controller cable 128. The camera 102 will operate (scan and transmit) given only power from the controller 122. Internal timing of the camera is in effect until an external start signal is detected by the camera. Upon detection of an external start signal, the camera automatically switches over to external line rate control.

The external start signal marks the beginning of the serial data transmission from the controller 122 to the camera 102. The transmitted data consists of one byte of command data, four bytes of web position data, and two bytes of external event data for a total of 7 bytes or 56 serial transmitted bits. The transmission of serial data is accompanied by a data clock. The external start signal remains high for the duration of valid serial data. Data is converted into byte form by the serial interface (part of 248) and loaded into a FIFO memory (also part of 248) for subsequent transmission to the computer processing unit 114.

It is to be noted that the computer processing necessary to evaluate the video and information signals and, ultimately, to evaluate the condition of the product being inspected, is described in detail in U.S. Pat. No. 4,752,897, issued Jun. 21, 1988, which patent is incorporated herein by reference.

In summary, the present invention provides a method for inspecting a moving web of product during manufacturing using a stationary linear array charge coupled device (CCD) camera, comprising the steps of exposing the linear array to light reflected from a surface of a linear segment of the web during an exposure time interval and creating a video signal corresponding to the surface of the linear segment, generating information signals related to the product, where the information signals are created external to the camera during the exposure time interval, transmitting both the video data signals and the information signals along at least one optical fiber to a computer processing unit during an exposure time interval, and processing the video data signals and the information signals to evaluate the condition of the product. An apparatus is also described and claimed to implement the method.

The foregoing description is included to illustrate the operation of the preferred embodiment and is not meant to limit the scope of the invention. The scope of the invention is to be limited only by the following claims. From the foregoing description, many variations will be apparent to those skilled in the art that would yet be encompassed by the spirit and scope of the invention.

Parts List For FIGS. 1–4

100=CAMERA SYSTEM
102=CAMERA
102a=LENS
106=JUNCTION BOX
108=FIBER OPTIC CABLE
110=JUNCTION BOX
112=RECEIVER BOARD
114=COMPUTER PROCESSING UNIT
116=OPTICAL FIBER
122=CAMERA CONTROLLER
128=CABLE
129=OPTICAL FIBER
130=EXTERNAL ENCODER INPUT SIGNAL
132=EXTERNAL ENCODER
133=INSPECTION PRODUCT
134=OPTICALLY ISOLATED DIGITAL I/O SIGNAL
202=CAMERA HOUSING
206=ARRAY BOARD
208=MOTHER BOARD
210=VIEWFINDER BOARD
212=VIDEO BOARD
214=TRANSMITTER BOARD
216=LINEAR ARRAY
218=RIBBON CABLE
220=VIEWFINDER CAMERA
221=PIN CONNECTOR
222=VIEWFINDER OUTPUT TERMINAL
224, 226=VIDEO SIGNAL INPUTS
228=VIDEO OUTPUT TERMINAL (VIDEO A)
230=VIDEO OUTPUT TERMINAL (VIDEO B)
234=FIBER OPTIC OUTPUT TERMINAL
238=AUXILIARY ACCESS
240=RESET ACCESS APERTURE
242=A/D CONVERTER
244=INTERNAL STATUS REGISTER
246=CHECKSUM DEVICES
248=SERIAL INTERFACE AND FIFO MEMORY
250=NULL DATA REGISTER
252=SEQUENCER
254=TRANSMITTER REGISTERS
256=HIGH SPEED FORMATTER
258=FIBER OPTIC TRANSMITTER
264=MULTIPLEXER

What is claimed is:

1. A method for inspecting a product, comprising:

scanning a surface of said product with a scanning device and creating scan lines each with video data signals corresponding to said surface, wherein each said scan line includes non-useful or dead (i.e., dark) video data signals;

generating information signals related to said product, wherein said information signals are created external to said scanning device;

transmitting both said video data signals and said information signals along at least one optical fiber to a computer processing unit, wherein said information signals are multiplexed into said non-useful or dead (i.e., dark) video data signals to create a sequential stream of data for transmission to said computer processing unit; and processing said video data signals and said information signals to evaluate the condition of said product.

2. A method as recited in claim 1 wherein said scanning device is a linear array charge coupled device (CCD) camera.

3. A method as recited in claim 2 wherein said product is moving and said camera is stationary during scanning.

4. A method as recited in claim 3 wherein said product is produced in continuous sheet form.

5. A method as recited in claim 4 wherein said information signals comprise information which indicates a beginning or end of said sheet.

6. A method as recited in claim 3 wherein said information signals comprise information about rate of change of position of the product.

7. A method as recited in claim 3 wherein said product is produced in discrete sheets and said information signals comprise a command issued to divert or sort said discrete sheets.

8. A method as recited in claim 1 wherein both said video data signals and said information signals are transmitted along a single optical fiber.

9. A method for inspecting a moving web of product during manufacturing using a stationary linear array charge coupled device (CCD) camera, comprising;
 a) exposing said linear array to light reflected from a surface of a linear segment of said web during an exposure time interval and creating scan lines each with video signals corresponding to said surface of said linear segment, wherein each said scan line includes non-useful or dead (i.e. dark) video data signals;
 b) generating information signals related to said product, wherein said information signals are created external to said camera during said exposure time interval;
 c) transmitting both said video data signals and said information signals along at least one optical fiber to a computer processing unit during an exposure time interval, wherein said information signals are multiplexed into said non-useful or dead (i.e., dark) video data signals to create a sequential stream of data for transmission to said computer processing unit; and,
 d) processing said video data signals and said information signals to evaluate the condition of said product.

10. A method as recited in claim 9 and further including repeating steps a) through d) as necessary until an entire product has been inspected.

11. A method as recited in claim 9 wherein said transmitting said video data signals and said information signals occurs during an immediately subsequent exposure time interval with respect to the exposure time interval during which said video and information signals were obtained.

12. A method as recited in claim 9 wherein said information signals comprise information about rate of change of position of the product.

13. A method as recited in claim 9 wherein said information signals comprise information which indicates a beginning or end of said web.

14. A method as recited in claim 9 wherein said information signals comprises a command issued to divert or sort said web.

15. A method as recited in claim 9 wherein both said video data signals and said information signals are transmitted along a single optical fiber.

16. An apparatus for inspecting a product, comprising:
 means for scanning a surface of said product and creating scan lines each with video data signals corresponding to said surface, wherein each said scan line includes non-useful or dead (i.e., dark) video data signals;
 means for generating information signals related to said product, wherein said information signals are created external to said means for scanning;
 means for transmitting both said video data signals and said information signals along at least one optical fiber, wherein said information signals are multiplexed into said non-useful or dead (i.e., dark) video data signals to create a sequential stream of data for transmission to said computer processing unit; and
 a computer processing unit to receive said video and information signals and operatively arranged to process said video data signals and said information signals to evaluate the condition of said product.

17. An apparatus as recited in claim 16 wherein said means for scanning is a linear array charge coupled device (CCD) camera.

18. An apparatus as recited in claim 17 wherein said product is moving and said camera is stationary during scanning.

19. An apparatus as recited in claim 18 wherein said product is produced in continuous sheet form.

20. An apparatus as recited in claim 19 wherein said information signals comprise information which indicates a beginning or end of said sheet.

21. An apparatus as recited in claim 19 wherein said product is produced in discrete sheets and said information signals comprise a command issued to divert or sort said discrete sheets.

22. An apparatus as recited in claim 18 wherein said information signals comprise information about rate of change of position of the product.

23. An apparatus as recited in claim 16 wherein both said video data signals and said information signals are transmitted along a single optical fiber.

24. An apparatus for inspecting a product during manufacturing using a stationary linear array charge coupled device (CCD) camera, comprising;
 a) a stationary linear array charge coupled device (CCD) camera having a linear array operatively arranged to be exposed to light reflected from a surface of a linear segment of said web during an exposure time interval and including means for creating scan lines each with video signals corresponding to said surface of said linear segment, wherein each said scan line includes non-useful or dead (i.e., dark) video data signals;
 b) means for generating information signals related to said product, wherein said information signals are created external to said camera during said exposure time interval;
 c) means for transmitting both said video data signals and said information signals along at least one optical fiber during an exposure time interval, wherein said information signals are multiplexed into said non-useful or dead (i.e., dark) video data signals to create a sequential stream of data for transmission to said computer processing unit; and,
 d) a computer processing unit operatively arranged to receive said video and information signals and to process said signals to evaluate the condition of said product.

25. An apparatus as recited in claim 24 wherein the entire surface of said product is scanned to evaluate the condition of said product.

26. An apparatus as recited in claim 24 wherein transmission of said video data signals and said information signals occurs during an immediately subsequent exposure time interval with respect to the exposure time interval during which said video and information signals were obtained.

27. An apparatus as recited in claim 24 wherein said information signals comprise information about rate of change of position of the product.

28. An apparatus as recited in claim 24 wherein said information signals comprise information which indicates a beginning or end of said product.

29. An apparatus as recited in claim 24 wherein said information signals comprises a command issued to divert or sort said product.

30. An apparatus as recited in claim 24 wherein both said video data signals and said information signals are transmitted along a single optical fiber.

31. An apparatus as recited in claim 24 wherein said product is a moving web.

* * * * *